US009018318B2

(12) United States Patent
Deglmann et al.

(10) Patent No.: US 9,018,318 B2
(45) Date of Patent: Apr. 28, 2015

(54) CATALYSTS FOR THE PREPARATION OF CARBONATES FROM EPOXIDES AND $CO_2$

(75) Inventors: Peter Deglmann, Mannheim (DE); Anna Katharina Brym, Limburgerhof (DE); Bernhard Rieger, München (DE); Maximilian Lehenmeier, München (DE); Stephan Klaus, München (DE)

(73) Assignee: BASF SE Corporation, Ludwigshafen (DE)

( * ) Notice: Subject to any disclaimer, the term of this patent is extended or adjusted under 35 U.S.C. 154(b) by 256 days.

(21) Appl. No.: 13/599,408

(22) Filed: Aug. 30, 2012

(65) Prior Publication Data
US 2013/0060001 A1 Mar. 7, 2013

Related U.S. Application Data

(60) Provisional application No. 61/530,415, filed on Sep. 2, 2011.

(51) Int. Cl.
*C08F 283/00* (2006.01)
*C07F 3/00* (2006.01)
*C08G 64/34* (2006.01)
*C07D 257/10* (2006.01)
*C07F 7/10* (2006.01)
*C08F 283/02* (2006.01)

(52) U.S. Cl.
CPC ............... *C07F 3/003* (2013.01); *C08G 64/34* (2013.01); *C07D 257/10* (2013.01); *C07F 7/10* (2013.01)

(58) Field of Classification Search
USPC ................ 528/405; 540/465, 472; 525/461
See application file for complete search history.

(56) References Cited

U.S. PATENT DOCUMENTS

| 4,943,677 | A | 7/1990 | Rokicki |
| 5,026,676 | A | 6/1991 | Motika et al. |

FOREIGN PATENT DOCUMENTS

| DE | 102004037201 B3 | 9/2005 |
| WO | WO-0008088 A1 | 2/2000 |

OTHER PUBLICATIONS

Synthesis, characterization and biological evaluation of macrocyclic Schiff bases with oxovanadium (V) complexes: Vatsala Pawar, Sunil joshi and V.Uma; Department of Chemistry, Government College, Ajmer, Rajasthan, India Der Pharma Chemica, 2010, 2(5):377-382 (http://derpharmachemica.com/archive.html).*
International Search Report(Partial) for PCT/EP2012/066931, dated Oct. 18, 2012.

Moore, et. al., "Mechanism of the Alternating Copolymerization of Epoxides and $CO_2$ Using β-Diiminate Zinc Catalysts: Evidence for a Bimetallic Epoxide Enchainment", *J. Am. Chem. Soc.*, vol. 125, (2003), pp. 11911-11924.
Lee et al., "Bimetallic Anilido-Aldimine Zinc Complexes for Epoxide/$CO_2$ Copolymerization", J. Am. Chem. Soc., 2005, vol. 127, pp. 3031-3037.
International Preliminary Report on Patentability, International Application No. PCT/EP2012/066931, International Filing Date Aug. 31, 2012.
Inoue, Shohei, et al., "Copolymerization of Carbon Dioxide and Epoxide with Organometallic Compounds", Die Makromolekulare Chemie, vol. 130, No. 3170, (1969), pp. 210-220.
Darensbourg, Donald J., et al., "Catalytic Activity of Zinc(ii) Phenoxides Which Possess Readily Accessible Coordination Sites. Copolymerization and Terpolymerization of Epoxides and Carbon Dioxide", Macromolecules, vol. 28, (1995), pp. 7577-7579.
Cheng, Ming, et al., "Catalytic Reactions Involving $C_1$ Feedstocks: New High-Activity Zn(II)-Based Catalysts for the Alternating Copolymerization of Carbon Dioxide and Epoxides", J. Am. Chem. Soc., vol. 120, (1998), pp. 11018-11019.
Bourget-Merle, Laurence, et al., Metal β-Diketiminates Revisited: *Ansa*-$CH_2$-Bridged Bis(β-Diketiminate)s of Lithium and Aluminum Having Diverse Structures, Journal of Organometallic Chemistry, vol. 689, (2004), pp. 4357-4365.
Vitanova, Daniela V., et al., "Rare Earth Metal Complexes Based on β-Diketiminato and Novel Linked Bis(β-Diketiminato) Ligands: Synthesis, Structural Characterization and Catalytic Application in Epoxide/$CO_2$-Copolymerization", Journal of Organometallic Chemistry, vol. 690, (2005), pp. 5182-5197.
Lee, Su Yeon, et al., "Syntheses and Structures of a Macrocyclic β-Diketimine and its Zinc and Copper Complexes", Organometallics, vol. 23, (2004), pp. 5382-5385.
Lee, Bun Yeoul et al., "Bimetallic Fluorine-Substituted Anilido-Aldimine Zinc Complexes for $CO_2$/(Cyclohexene Oxide) Copolymerization", Inorg. Chem., vol. 45, (2006), pp. 4228-4237.
Limberg, Christian, et al., "Dinuclear Zinc Complexes Based on Parallel β-Diiminato Binding Sites: Syntheses, Structures, and Properties as $CO_2$/Epoxide Copolymerization Catalysts", Organometallics, vol. 26, (2007), pp. 3668-3676.
Harder, Sjoerd, et al., "Bimetallic Calcium and Zinc Complexes with Bridged β-Diketiminate Ligands: Investigations on Epoxide/$CO_2$ Copolymerization", Organometallics, vol. 27, (2008), pp. 6178-6187.

* cited by examiner

*Primary Examiner* — Terressa Boykin
(74) *Attorney, Agent, or Firm* — Drinker Biddle & Reath LLP

(57) ABSTRACT

A macrocycle based on β-diketimines, a process for preparing the inventive macrocycle, an uncharged macrocyclic dimetallic complex based on the inventive macrocycle, and a process for preparing the uncharged macrocyclic dimetallic complex, the use of the uncharged macrocyclic dimetallic complex as a polymerization catalyst in the polymerization of carbon dioxide with one or more epoxides, a process for preparing polycarbonates by reacting carbon dioxide with one or more epoxides in the presence of the inventive uncharged macrocyclic dimetallic complex, and a polycarbonate prepared by the process according to the invention.

8 Claims, No Drawings

CATALYSTS FOR THE PREPARATION OF CARBONATES FROM EPOXIDES AND CO$_2$

CROSS-REFERENCE TO RELATED APPLICATIONS

This application claims benefit under 35 U.S.C. § 119(e) of U.S. Provisional Patent App. Ser. No. 61/530,415, filed September 2, 2011, which is incorporated herein by reference in its entirety.

The present invention relates to a macrocycle based on β-diketimines, a process for preparing the inventive macrocycle, an uncharged macrocyclic dimetallic complex based on the inventive macrocycle, and a process for preparing the uncharged macrocyclic dimetallic complex, the use of the uncharged macrocyclic dimetallic complex as a polymerization catalyst in the polymerization of carbon dioxide with one or more epoxides, a process for preparing polycarbonates by reacting carbon dioxide with one or more epoxides in the presence of the inventive uncharged macrocyclic dimetallic complex, and a polycarbonate prepared by the process according to the invention.

Polycarbonates can be prepared by copolymerization of epoxides and carbon dioxide. They are therefore of interest as biologically renewable polymers which are prepared proceeding from renewable raw materials. In addition, polycarbonates are of interest as biodegradable polymers for applications, for example, in pharmaceuticals, agriculture, or as specialty chemicals. Polycarbonates are of particular interest as packaging materials.

The reaction of epoxides with carbon dioxide is known in the prior art. Without use of a catalyst, this reaction basically does not proceed. The literature describes various catalysts or catalyst systems for preparation of polycarbonates.

Inoue et al., Makromol. Chem—1969, 130, 210 describes the alternating copolymerization of epoxides with carbon dioxide in the presence of a heterogeneous mixture of diethylzinc and water. However, this catalyst system is of very low activity, and the resulting polypropylene carbonate exhibits high polydispersities and an irregular structure.

U.S. Pat. Nos. 4,943,677 and 5,026,676 describe the preparation of poly(alkylene carbonates) by copolymerization of carbon dioxide and epoxides in the presence of zinc polycarboxylate catalysts. The catalysts are preferably prepared by reaction of zinc oxide and a dicarboxylic acid, e.g. glutaric acid or adipic acid.

Darensbourg et al., Makromolecules 1995, 28, 7577 describes di(phenoxide)-zinc complexes suitable for alternating copolymerization of epoxides with CO$_2$, which are obtainable by reaction of 2,6-disubstituted or 2,4,6-trisubstituted phenols with Zn[N(SiMe$_3$)$_2$]$_2$. This catalyst system, however, is only of moderate activity, and the polymers obtained exhibit high polydispersities.

Cheng et al., J. Am. Chem. Soc. 1998, 120, 11018 discloses β-diketiminate-zinc single site catalysts. These are suitable for alternating copolymerization of carbon dioxide and epoxides. It is stated that a high polymerization activity was achieved.

Similar β-diketiminate-zinc catalysts are disclosed in WO 00/08088. These catalysts are likewise used for alternating copolymerization of epoxides and carbon dioxide, and exhibit a high polymerization activity.

β-Diketiminate-zinc complexes are thus one of the most promising catalyst groups at present for alternating copolymerization of epoxides with carbon dioxide.

It is an object of the present invention to provide further high-activity catalysts suitable for alternating copolymerization of epoxides with carbon dioxide, which are suitable for copolymerization and terpolymerization of various epoxides with carbon dioxide and lead to polycarbonates with a low polyether content and a low polydispersity.

This object is achieved by the macrocyclic bimetallic β-diketiminate-zinc complexes specified hereinafter.

Bridged bis(β-diketiminate) complexes are described in L. Bourget-Merle et al., J. Organomet Chem. 2004, 689, 4357 and D. V. Vitanova et al., J. Organomet. Chem. 2005, 690, 5182.

Lee et al, Organometallics 2004, 23, 5382-5385 describes macrocyclic β-diketimines and the zinc and copper complexes thereof. The macrocyclic β-diketimines have an aromatic bridge.

Lee et al., Inorg. Chem. 2006, 45, 4228-4237 relates to bimetallic fluorine-substituted anilido-aldimine-zinc complexes for copolymerization of CO$_2$ and cyclohexene oxide. The macrocyclic complexes have one aromatic bridge.

Limberg et al., Organometallics 2007, 26, 3668-3676 describes dinuclear zinc complexes based on parallel β-diketiminato binding sites. The complexes are used as catalysts in the copolymerization of CO$_2$ and cyclohexene oxide.

Harder et al. relates to bimetallic calcium and zinc complexes which have bridged diketiminate ligands. The catalysts are used in the copolymerization of CO$_2$ and cyclohexene oxide.

The present invention provides bimetallic zinc complexes based on a macrocyclic ligand of the general formula (I). These bimetallic zinc complexes are suitable for preparation of carbonates from epoxides and carbon dioxide, exhibiting a high activity and being suitable for preparation of polycarbonates with a low polydispersity and a small amount of polyether linkages.

The present invention further provides a macrocycle which forms the basis of the inventive bimetallic zinc complex.

The present invention thus relates, in a first embodiment, to a macrocycle of the general formula (I)

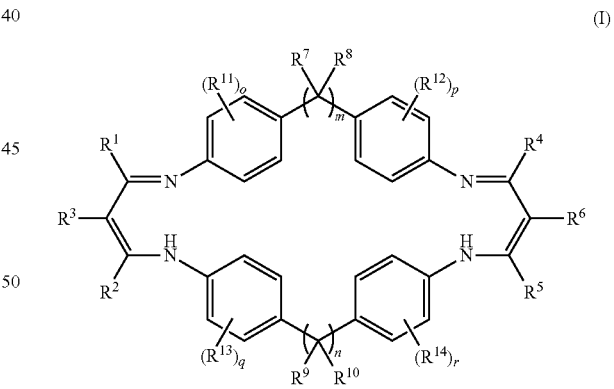

in which $R^1$, $R^2$, $R^4$, $R^5$ are each independently H, $C_1$-$C_{10}$-alkyl, $C_1$-$C_{10}$-fluoroalkyl, $C_1$-$C_{10}$-alkoxy or $C_6$-$C_{20}$-aryl; preferably hydrogen, $C_1$-$C_4$-alkyl, $C_1$-$C_4$-fluoroalkyl, preferably $CF_3$, $CHF_2$, $CH_2F$; $C_2F_5$, $C_2HF_4$, $C_2H_2F_3$, $C_2H_3F_2$, $C_2H_4F$, $C_6$-$C_{20}$-fluoroaryl or $C_1$-$C_4$-alkoxy; more preferably hydrogen, methyl, ethyl, n-propyl, isopropyl, $CF_3$, $C_2F_5$, methoxy or ethoxy; most preferably methyl;

$R^3$, $R^6$ are each independently H, $C_1$-$C_{10}$-alkyl, $C_6$-$C_{20}$-aryl, halogen radical, e.g. F, Cl, Br, I, pseudohalogen radical, e.g. CN, SCN, carboxylic acid radical, e.g. $R^a$(CO)—O— or $R^b$—O—(CO)— in which $R^a$ and $R^b$ are each independently $C_1$-$C_{10}$-alkyl, preferably $C_1$-$C_4$-alkyl, more preferably methyl, ethyl, n-propyl or isopropyl, or sulfonyl group, e.g. $R^c$—$SO_2$— in which $R^c$ is $C_1$-$C_{10}$-alkyl, preferably $C_1$-$C_4$-alkyl, more preferably methyl, ethyl, n-propyl or isopropyl; preferably hydrogen, $C_1$-$C_4$-alkyl, Cl, Br, CN, SCN, $R^a(CO)$—O—, $R^b$—O—C(O)—, in which $R^a$ and $R^b$ are each independently methyl, ethyl, n-propyl or isopropyl, or $R^c$—$SO_2$— in which $R^c$ is methyl, ethyl, n-propyl or isopropyl; more preferably hydrogen, methyl, ethyl, n-propyl or isopropyl, CN, Cl, $CH_3C(O)$—O—, $CH_3$—O—C(O)— or $CH_2$—$SO_2$; most preferably H;

$R^7$, $R^8$, $R^9$, $R^{10}$ are each independently H, $C_1$-$C_{10}$-alkyl, $C_1$-$C_{10}$-fluoroalkyl, $C_1$-$C_{10}$-alkoxy or $C_6$-$C_{20}$-aryl; preferably hydrogen, $C_1$-$C_4$-alkyl, $C_1$-$C_4$-fluoroalkyl or $C_1$-$C_4$-alkoxy; more preferably hydrogen, methyl, ethyl, n-propyl, isopropyl, $CF_{32}C_2F_5$, methoxy or ethoxy; most preferably H;

$R^{11}$, $R^{12}$, $R^{13}$, $R^{14}$ are each independently H, $C_1$-$C_{10}$-alkyl, $C_1$-$C_{10}$-fluoroalkyl, $C_6$-$C_{20}$-aryl, halogen, pseudohalogen, $C_1$-$C_{10}$-alkoxy or $C_6$-$C_{20}$-aryloxy; preferably hydrogen, $C_1$-$C_4$-alkyl, $C_1$-$C_4$-fluoroalkyl, Cl, Br, CN or O—$C_1$-$C_4$-alkyl; more preferably hydrogen;

m, n are each independently 1 to 20, preferably 1 to 10, more preferably 1, 2, 3 or 4; even more preferably 1 or 2; very especially preferably 1;

o, p, q, r are each independently 0, 1, 2, 3 or 4; preferably 0, 1, 2 or 3; more preferably 0, 1 or 2; most preferably 0 or 1.

A very particularly preferred macrocycle has the following formula (Ia):

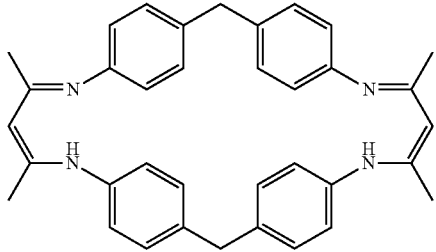

(Ia)

The inventive macrocycle of the general formula (I) is suitable for preparation of bimetallic complexes, where the metal atoms in the bimetallic complexes have defined distances from one another.

The macrocycle of the general formula (I) can be prepared proceeding from the corresponding β-diketones of the general formula (IIa) or (IIb)

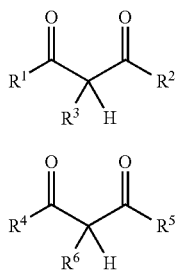

in which
$R^1$, $R^2$ and $R^4$, $R^5$ are each independently H, $C_1$-$C_{10}$-alkyl, $C_1$-$C_{10}$-fluoroalkyl, $C_1$-$C_{10}$-alkoxy or $C_6$-$C_{20}$-aryl; preferably hydrogen, $C_1$-$C_4$-alkyl, $C_1$-$C_4$-fluoroalkyl, preferably $CF_3$, $CHF_2$, $CH_2F$; $C_2F_5$, $C_2HF_4$, $C_2H_2F_3$, $C_2H_3F_2$, $C_2H_4F$, $C_6$-$C_{20}$-fluoroaryl or $C_1$-$C_4$-alkoxy; more preferably hydrogen, methyl, ethyl, n-propyl, isopropyl, $CF_3$, $C_2F_5$, methoxy or ethoxy; most preferably methyl;

$R^3$ and $R^6$ are each independently H, $C_1$-$C_{10}$-alkyl, $C_6$-$C_{20}$-aryl, halogen radical, e.g. F, Cl, Br, I, pseudohalogen radical, e.g. CN, SCN, carboxylic acid radical, e.g. $R^a(CO)$—O— or $R^b$—O—(CO)— in which $R^a$ and $R^b$ are each independently $C_1$-$C_{10}$-alkyl, preferably $C_1$-$C_4$-alkyl, more preferably methyl, ethyl, n-propyl or isopropyl, or sulfonyl group, e.g. $R^c$—$SO_2$— in which $R^c$ is $C_1$-$C_{10}$-alkyl, preferably $C_1$-$C_4$-alkyl, more preferably methyl, ethyl, n-propyl or isopropyl; preferably hydrogen, $C_1$-$C_4$-alkyl, Cl, Br, CN, SCN, $R^a(CO)$—O—, $R^b$—O—C(O)—, in which $R^a$ and $R^b$ are each independently methyl, ethyl, n-propyl or isopropyl, or $R^c$—$SO_2$— in which $R^c$ is methyl, ethyl, n-propyl or isopropyl; more preferably hydrogen, methyl, ethyl, n-propyl or isopropyl, CN, Cl, $CH_3C(O)$—O—, $CH_3$—O—C(O)— or $CH_3$—$SO_2$; most preferably H.

Especially preferably, acetylacetone is used both as the β-diketone (IIa) and as the β-diketone (IIb).

Preference is given to preparing the inventive macrocycle of the formula (I) proceeding from the β-diketone of the formula (IIa) in two stages.

1st stage: Reaction of the β-diketone compounds of the general formulae (IIa) and (IIb) with a diaminodiphenyl compound of the general formula (IIIa) to give a compound of the general formula (IV)

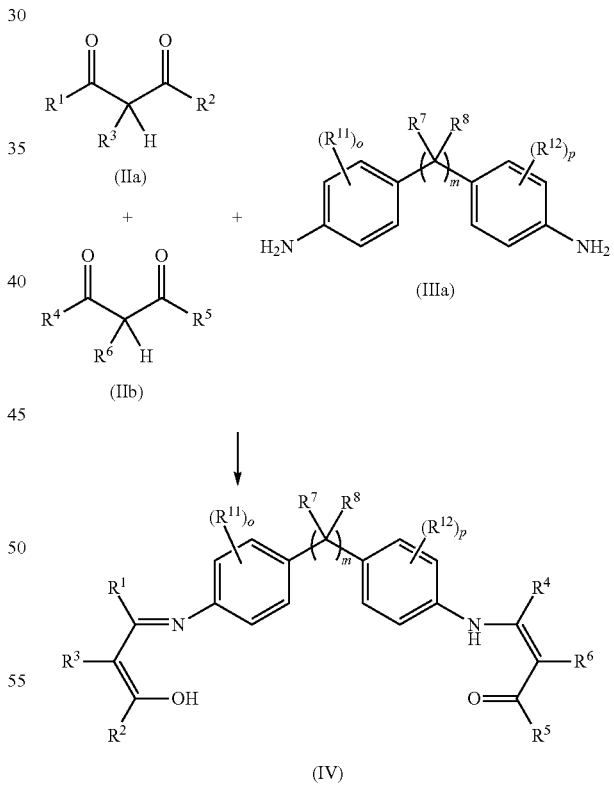

in which:
$R^7$, $R^8$ are each independently H, $C_1$-$C_{10}$-alkyl, $C_1$-$C_{10}$-fluoroalkyl, $C_1$-$C_{10}$-alkoxy or $C_6$-$C_{20}$-aryl; preferably hydrogen, $C_1$-$C_4$-alkyl, $C_1$-$C_4$-fluoroalkyl or $C_1$-$C_4$-alkoxy; more preferably hydrogen, methyl, ethyl, n-propyl, isopropyl, $CF_{32}C_2F_5$, methoxy or ethoxy; most preferably H;

$R^{11}$, $R^{12}$ are each independently H, $C_1$-$C_{10}$-alkyl, $C_1$-$C_{10}$-fluoroalkyl, $C_6$-$C_{20}$-aryl, halogen, pseudohalogen, $C_1$-$C_{10}$-alkoxy or $C_6$-$C_{20}$-aryloxy; preferably hydrogen, $C_1$-$C_4$-alkyl, $C_1$-$C_4$-fluoroalkyl, Cl, Br, CN or O—$C_1$-$C_4$-alkyl; more preferably hydrogen;

m is independently 1 to 20, preferably 1 to 10, more preferably 1, 2, 3 or 4; even more preferably 1 or 2; very especially preferably 1;

o, p are each independently 0, 1, 2, 3 or 4; preferably 0, 1, 2 or 3; more preferably 0, 1 or 2; most preferably 0 or 1; and the $R^1$, $R^2$ and $R^3$ radicals and the $R^4$, $R^5$ and $R^6$ radicals are each as defined above for the formulae (IIa) and (IIb).

The β-diketo compounds of the formulae (IIa) and (IIb) may be the same or different, and are preferably the same.

The β-diketo compounds of the formulae (IIa) and (IIb) are reacted with the diaminodiphenyl compound of the formula (IIIa) generally in the presence of an acidic catalyst. Suitable acidic catalysts are known to those skilled in the art. For example, aromatic and aliphatic carboxylic acids and sulfonic acids are suitable, such as formic acid, acetic acid, benzenesulfonic acid or toluenesulfonic acid. A preferred example of a suitable acidic catalyst is para-toluenesulfonic acid (p-TsOH).

The catalyst is generally used in an amount of 0.01 to 0.5 molar equivalent, preferably 0.02 to 0.1 molar equivalent, more preferably 0.03 to 0.07 molar equivalent, based on the diaminodiphenyl compound of the general formula (IV).

Typically, the first stage is performed in a solvent, preference being given to organic solvents. Particularly preferred organic solvents are aromatic compounds, most preferably toluene or benzene.

The molar ratio of the β-diketo compounds of the general formulae (IIa) and (IIb) (sum of the molar proportions of compounds (IIa) and (IIb), where the molar ratio of compounds (IIa) and (IIb) is generally 0.8 to 1.2:0.8 to 1.2, preferably 0.9 to 1.1:0.9 to 1.1, more preferably 1:1) to the diaminodiphenyl compound of the general formula (IIIa) is generally 1.8 to 10:1, preferably 1.9 to 5:1, more preferably 1.9 to 2.1:1.

The reaction in stage 1 is generally performed at a temperature of 60 to 160° C., preferably 70 to 150° C., more preferably 80 to 140° C. In general, the reaction is effected at standard pressure. The reaction time is typically 1 to 16 hours, preferably 1.5 to 8 hours, more preferably 2 to 3 hours.

After the reaction, the reaction product obtained in stage 1 is worked up and isolated by processes known to those skilled in the art. For example, the resulting reaction mixture is washed with a basic solution, e.g. $NaHCO_3$ solution, the organic phase is removed and then the solvent is removed (from the organic phase), preferably under reduced pressure. The resulting residue can then be resuspended, for example in hexane, in which case—preferably after subsequent filtration—the desired product is typically obtained in the form of a solid.

2nd stage: Reaction of the reaction product from the first stage of the general formula (IV) with a further diaminodiphenyl compound of the general formula (V) to obtain a macrocycle of the general formula (I)

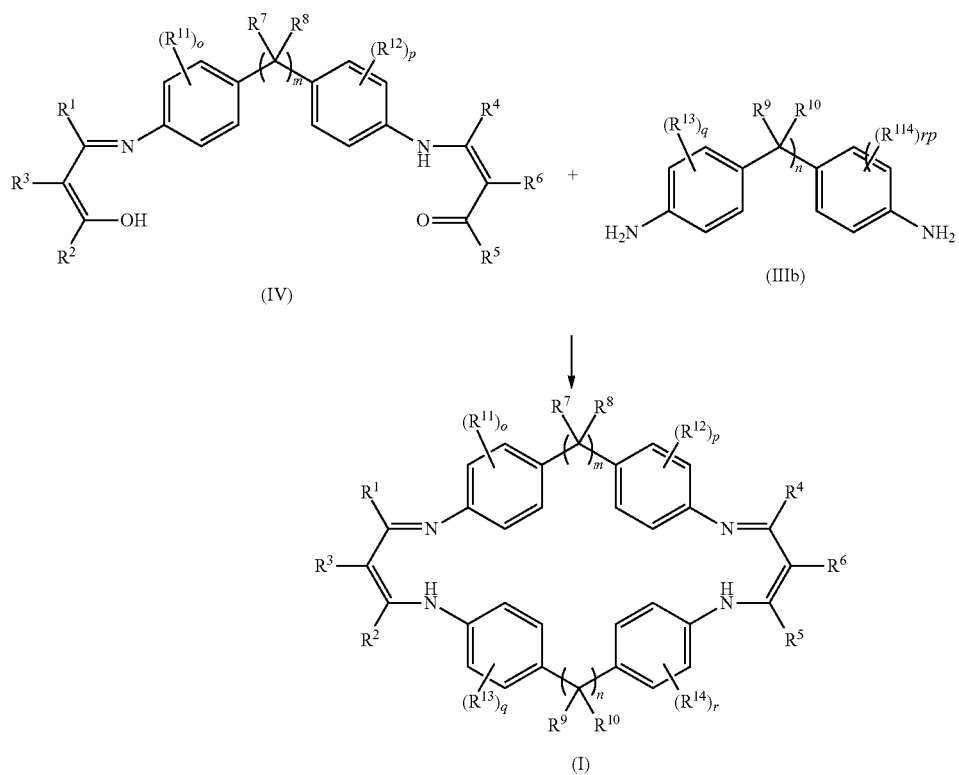

in which the radicals and indices $R^1$, $R^2$, $R^4$, $R^5$, $R^3$, $R^6$, $R^7$, $R^8$, $R^{11}$, $R^{12}$, m, o and p are each as defined for stage 1 and the $R^9$ and $R^{10}$ radicals are each independently as defined for the $R^7$ and $R^8$ radicals, the $R^{13}$ and $R^{14}$ radicals are each independently as defined for the $R^{11}$ and $R^{12}$ radicals, n, independently of m, is as defined for m, and q and r are each independently as defined for o and p.

The reaction in the second stage (ring closure) is effected—like the first stage—in the presence of acid. The acids specified for stage 1 are suitable here in principle. It is additionally possible and preferred to use a diaminodiphenyl compound of the formula (IIIb) to which two molecules of HCl are coordinated.

The second stage of the process according to the invention for preparation of the inventive macrocycle is preferably performed in a solvent. Suitable solvents are, for example, alcohols, especially ethanol, n-propanol and isopropanol.

The molar ratio between the reaction product from the first stage of the formula (IV) and the diaminodiphenyl compound of the general formula (IIIb) is generally 0.7 to 1.3:1, preferably 0.8 to 1.2:1, more preferably 0.9 to 1.1:1.

The second stage is performed at a temperature of 40 to 120° C., preferably 50 to 110° C., more preferably 60 to 100° C., typically at standard pressure.

The reaction time is 1 to 48 hours, preferably 4 to 24 hours, more preferably 8 to 16 hours.

The resulting reaction product is worked up by processes known to those skilled in the art. For example, the precipitate which generally forms is dissolved in water, and the desired amine of the diketiminate macrocycle of the formula (I) is released by adding a basic compound, e.g. $NaHCO_3$. Subsequently, the desired macrocycle of the formula (I) is extracted with an organic solvent, e.g. methylene chloride, and isolated by removing the solvent. For further purification, the desired macrocycle of the formula (I) can be recrystallized, for example from toluene, to obtain the desired macrocycle of the general formula (I), generally in the form of a solid.

The macrocycle of the general formula (I) is especially suitable for preparation of macrocyclic dimetallic complexes. These macrocyclic dimetallic complexes can be used, for example, as catalysts in the polymerization of epoxides with carbon dioxide to prepare polycarbonates.

The present application therefore further provides an uncharged macrocyclic dimetallic complex of the general formula (V)

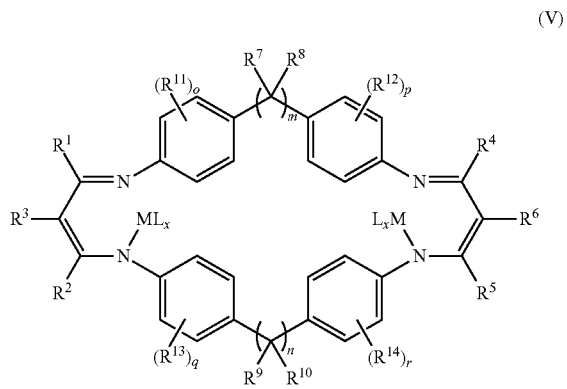

(V)

in which

M is a metal of group 6, 8, 9, 10, 11 or 12 of the periodic table of the elements (IUPAC nomenclature), preferably Cr, Fe, Co, Cu or Zn, more preferably Cu or Zn, most preferably Zn;

L is a monodentate, singly negatively charged ligand; preferably $-N(SiMe_3)_2$, $-OAc$, $-OR^{15}$, $-SO_2R^{15}$, halogen such as F, Cl or Br, or hydrogen; more preferably $-N(SiMe_3)_2$;

x, depending on the oxidation state and coordination number of the metal M, is 0, 1, 2 or 3, preferably 0, 1 or 2; more preferably—in the case that the oxidation state of the metal is II-1;

$R^{15}$ is $C_1$-$C_{10}$-alkyl or $C_6$-$C_{20}$-aryl, preferably $C_1$-$C_4$-alkyl; more preferably methyl, ethyl, n-propyl or isopropyl;

and the radicals and indices $R^1$, $R^2$, $R^4$, $R^5$, $R^3$, $R^6$, $R^7$, $R^8$, $R^9$, $R^{10}$, $R^{11}$, $R^{12}$, $R^{13}$, $R^{14}$, m, n, o, p, q and r are each as defined for the macrocycle of the general formula (I).

The inventive uncharged macrocyclic dimetallic complex of the general formula (V) is especially suitable as a catalyst for preparation of polycarbonates from epoxides and carbon dioxide. The catalyst is highly active, and it is possible to prepare polycarbonates with narrow molecular weight distribution and a small number of polyether linkages.

The inventive uncharged macrocyclic dimetallic complex of the general formula (V) can be prepared by reacting the inventive macrocycle of the general formula (I) with a metal compound of the general formula (VI)

$$M(L_x)_2 \qquad (VI)$$

in which

M is a metal of group 6, 8, 9, 10, 11 or 12 of the periodic table of the elements (IUPAC nomenclature), preferably Cr, Fe, Co, Cu or Zn; more preferably Cu or Zn, most preferably Zn;

L is a monodentate, singly negatively charged ligand, preferably $-N(SiMe_3)_2$, $-OAc$, $-OR^{15}$, $-SO_2R^{15}$, halogen such as F, Cl or Br, or hydrogen, more preferably $-N(SiMe_3)_2$;

x, depending on the oxidation state and coordination number of the metal M, is 0, 1, 2 or 3; preferably 0, 1 or 2, more preferably—in the case that the oxidation state of the metal M is II-1;

$R^{15}$ is $C_1$-$C_{10}$-alkyl or $C_6$-$C_{20}$-aryl; preferably $C_1$-$C_4$-alkyl; more preferably methyl, ethyl, n-propyl or isopropyl.

The metal compounds of the formula (VI) are commercially available or are preparable by processes known to those skilled in the art.

The conversion of the macrocycle of the formula (I) to the uncharged macrocyclic dimetallic complex of the general formula (V) is generally performed in a solvent. Preferred solvents are organic solvents, more preferably aromatic organic solvents, e.g. toluene or benzene. The macrocycle of the general formula (I) is first dissolved in the aforementioned solvent.

Then the metal compound of the formula (VI) is added. In general, the molar ratio of the metal compound of the general formula (VI) to the macrocycle of the general formula (I) is 1.7 to 2.3:1 (molar ratio), preferably 1.8 to 2.2:1, more preferably 1.9 to 2.1:1.

The reaction mixture is generally stirred for a period of 8 to 24 hours, preferably 20 to 24 hours, more preferably 22 to 24 hours.

The reaction temperature is generally 50 to 130° C., preferably 60 to 120° C., more preferably 70 to 110° C.

The desired uncharged macrocyclic dimetallic complex of the formula (I) is obtained by removing the solvent, preferably under reduced pressure.

More preferably, the uncharged macrocyclic dimetallic complex of the formula (V) is a dinuclear zinc complex, i.e. M in the complex of the formula (V) is Zn. Most preferably, the complex is a dinuclear trimethylsilylamide-zinc complex, i.e. the -$ML_x$ group in the complex of the formula (V) is —ZnN$(SiMe_3)_2$ (where the $SiMe_3$ group can be abbreviated to TMS).

More preferably, the inventive uncharged macrocyclic dimetallic complex of the formula (V) has the formula (Va)

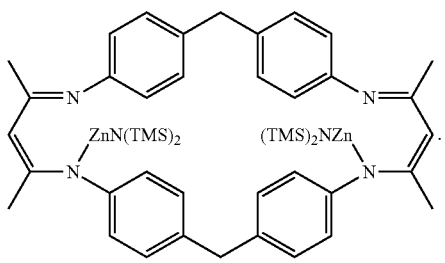

(Va)

The inventive uncharged macrocyclic dimetallic complex of the general formula (V) is suitable as a polymerization catalyst. More particularly, the uncharged macrocyclic dimetallic complex of the general formula (V) is suitable as a polymerization catalyst in the polymerization of carbon dioxide with one or more epoxides.

The present application therefore further provides for the use of the uncharged macrocyclic dimetallic complex of the general formula (V) as a polymerization catalyst in the polymerization of carbon dioxide with one or more epoxides. More preferably, the dinuclear zinc catalyst of the general formula (Va) specified above as particularly preferred is used as a polymerization catalyst in the polymerization of carbon dioxide with one or more epoxides.

Suitable epoxides are ethylene oxide and substituted epoxides. These are typically those compounds which are covered by the following general formula (VII):

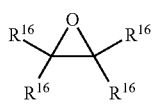

(VII)

In this formula, the $R^{16}$ radicals are each independently hydrogen, halogen, nitro group, cyano group, ester group, $C_1$-$C_{20}$-alkyl, $C_2$-$C_{20}$-alkenyl, $C_3$-$C_{20}$-cycloalkyl, $C_6$-$C_{20}$-aryl, $C_7$-$C_{20}$-aralkyl, $C_1$-$C_{20}$-alkoxy,
and/or two $R^{16}$ radicals may, if they are on different carbon atoms of the epoxy group, be bridged to one another and thus form a $C_3$-$C_{20}$-cycloalkylene group.

Preferred epoxides are selected from the group consisting of ethylene oxide, propylene oxide, butylene oxide, cyclopentene oxide, cyclohexene oxide, cycloheptene oxide, 2,3-epoxypropyl phenyl ether, epichlorohydrin, epibromohydrin, i-butene oxide, styrene oxide, glycidyl ether, glydidyl ester and acryloyl oxides. More preferably, the epoxides are selected from the group consisting of ethylene oxide, propylene oxide, butylene oxide, cyclopentene oxide, cyclohexene oxide and isobutene oxide. Very particular preference is given to propylene oxide and cyclohexene oxide. It is possible that one or more, for example two or three, of the aforementioned epoxides are used in the polymerization process, for example propylene oxide alone or cyclohexene oxide alone, or propylene oxide and cyclohexene oxide. It is thus possible in the polymerization process according to the invention to obtain polycarbonates in the form of copolymers or terpolymers.

The aforementioned epoxides can be prepared by processes known to those skilled in the art. For example, the epoxides can be obtained by epoxidation proceeding from terminal olefins. If the epoxidation proceeds in a non-stereospecific manner, an optical resolution should preferably be undertaken. It is, however, likewise possible to use the epoxides in the form of racemates thereof (in any desired ratios). Methods for optical resolution, for example by means of HPLC chromatography with chiral column material, are known to those skilled in the art. Advantageously, the epoxides are prepared proceeding from a terminal olefin via established stereoselective processes directly in enantiomerically pure or in optically enriched form. One example of a suitable process is what is called the Sharpless epoxidation (J. Am. Chem. Soc. 1987 (109), p. 5765 ff. and 8120 ff.).

In addition, optically enriched oxirane compounds are obtained via a process described in Jacobsen et al. (Tetrahedron Lett. 1997, 38, pages 773 to 776; and J. Org. Chem. 1998, 63, pages 6776 to 6777), proceeding from terminal olefins or racemic terminal epoxides. The processes are also simple to perform on the industrial scale (see, for example, Acc. Chem. Res. 2000, 33, pages 421 to 431).

It is also possible to prepare optically enriched oxirane compounds by adding the racemate in an appropriate amount to the enantiomerically pure oxirane compound.

Useful compounds with terminal double bonds are in principle all olefins of this compound class, e.g. propene, 1-butene, 1-pentene, 1-hexene, 1-heptene or 1-octene.

The present application further provides a process for preparing polycarbonates by reacting carbon dioxide with one or more epoxides in the presence of an uncharged macrocyclic dimetallic complex of the formula (V) or prepared by the process according to the invention for preparing the uncharged macrocyclic dimetallic complex of the formula (V).

Suitable and preferred epoxides and suitable and preferred uncharged macrocyclic dimetallic complexes of the formula (V) have already been specified above.

Particular preference is given to using, in the processes according to the invention, propylene oxide and/or cyclohexene oxide as epoxides.

In general, the uncharged macrocyclic dimetallic complex of the formula (V), which is preferably a dinuclear zinc catalyst, is used in an amount of 0.0001 to 0.05 mol %, preferably 0.0002 to 0.03 mol %, more preferably 0.0003 to 0.015 mol %, based on the total amount of the epoxide(s) used. The use of a cocatalyst is generally not required.

Typically, the process according to the invention is performed at a temperature of 18° C. to 160° C., preferably 20 to 170° C., more preferably 22 to 140° C.

The process according to the invention is generally performed at a $CO_2$ pressure of 1 to 80 bar, preferably 30 to 60 bar, more preferably 5 to 50 bar.

The exact setting of pressure and temperature depends firstly on the epoxide(s) to be polymerized, and on the particular temperature or the particular pressure.

The reaction time is generally 0.5 to 8 h, preferably 0.6 to 4 h, more preferably 0.7 to 2 h.

In general, the process according to the invention is performed in the absence of additional solvent. Typically, the epoxide(s) used is/are used as solvent.

To end the polymerization, an alcohol, especially methanol, is typically added. Subsequently, the resulting precipitate is generally dissolved in an organic solvent, e.g. methylene chloride. The organic phase can then be washed, for example, with dilute hydrochloric acid and subsequently concentrated. The desired polymer is subsequently precipitated, for example in an alcohol, e.g. methanol.

In a preferred embodiment of the process according to the invention, the reaction is conducted by dissolving the uncharged macrocyclic dimetallic complex of the formula (V) in the epoxide(s) to be polymerized, establishing the reaction pressure with carbon dioxide and then establishing the desired reaction temperature, or establishing the desired reaction temperature and then establishing the reaction pressure with carbon dioxide.

The polycarbonates prepared by the process according to the invention are notable for high molecular weights. The number-average molecular weight $M_n$ of the polycarbonates prepared by the process according to the invention is generally 30 to 50 kDa. The number-average molecular weight is determined by means of gel permeation chromatography (GPC, also referred to as Size Exclusion Chromatography (SEC)), using hexafluoroisopropanol (HFiP) as the eluent and calibration with polymethyl methacrylate (PMMA) standards. The procedure may be, for example, as follows: Detector: ERC 7510 differential refractometer from ERC; columns: HFiP gel precolumn and HFiP gel linear separating column, both from Polymer Laboratories; calibration with narrow-distribution PMMA standards with molecular weights M from 505 to 2 740 000 from PSS.

The polycarbonates prepared by the process according to the invention are additionally notable in that they have a low polyether content. The polyether content is the content of polyether linkages in the polymer. This is generally not more than 50 mol %, preferably 0.1 to 50 mol %, more preferably 0.2 to 30 mol %, even more preferably 0.3 to 10 mol %, very especially preferably 1 to 8 mol %.

The present invention therefore further provides a polycarbonate prepared by the process according to the invention. Preferred polycarbonates are selected from the group consisting of polypropylene carbonate, polycyclohexene carbonate and poly(propylene-cyclohexene) carbonate.

A great advantage of the inventive uncharged macrocyclic dimetallic complexes of the formula (V), especially of the dinuclear zinc complexes, is that it is possible to provide catalysts which are highly active for preparation of polycarbonates from one or more epoxides and carbon dioxide and, without addition of cocatalysts, can polymerize both alicyclic epoxides, e.g. propylene oxide, and cyclic epoxides, e.g. cyclohexene oxide, and mixtures of alicyclic and cyclic epoxides.

The polycarbonates obtained by means of the inventive uncharged macrocyclic dimetallic complexes of the formula (V) as catalysts are notable for a low proportion of polyether linkages and high molecular weights.

The examples which follow provide additional illustration of the invention.

EXAMPLES

Example 1

Ligand and Complex Synthesis

1st Stage: Preparation of the Compound of the Formula (3)

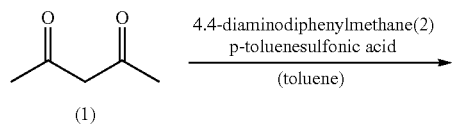

(1)

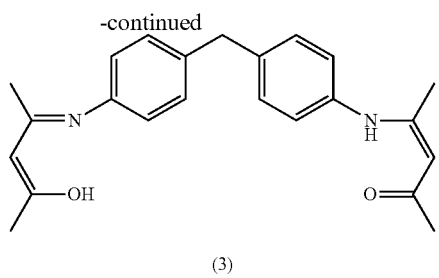

(3)

Synthesis of Compound (3)

4,4-Diaminodiphenylmethane (2) (5.79 g, 29.21 mmol, 0.5 eq.) is dissolved in toluene (50.00 mL), acetylacetone (1) (6.00 mL, 58.43 mmol, 1.0 eq.) and para-toluenesulfonic acid (p-TsOH) (0.50 g, 2.92 mmol, 0.05 eq) are added, and the mixture is boiled on a water separator overnight (16 hours). A reaction time of 2 hours is generally sufficient. The reaction mixture is washed with $NaHCO_3$ solution. The solvent is removed under reduced pressure and the residue is resuspended in hexane; after filtration, a solid (90%) is obtained.

| | Molar mass [g/mol] | Density [g/cm³] | Mass [g] | Volume [ml] | Amount [mmol] | Molar equivalents |
|---|---|---|---|---|---|---|
| acetylacetone | 100.12 | 0.975 | 5.85 | 6.00 | 58.43 | 1.00 |
| 4,4-diamino-Diphenylmethane | 198.26 | | 5.79 | | 29.21 | 0.50 |
| p-TsOH | 172.2 | | 0.50 | | 2.92 | 0.05 |
| toluene | | | | 50.00 | | |

Analysis $^1$H NMR ($CDCl_3$, 295.5 K, 300.13 MHz): δ=12.42 (s, 2H), 7.12 (d, $^3J$=8.3 Hz, 4H), 7.01 (d, $^3J$=8.3 Hz, 4H), 5.15 (s, 2H), 3.90 (s, 2H), 2.06 (s, 6H), 1.95 (s, 6H).

2nd Stage: Ring Closure to Give the Compound of the Formula (4)

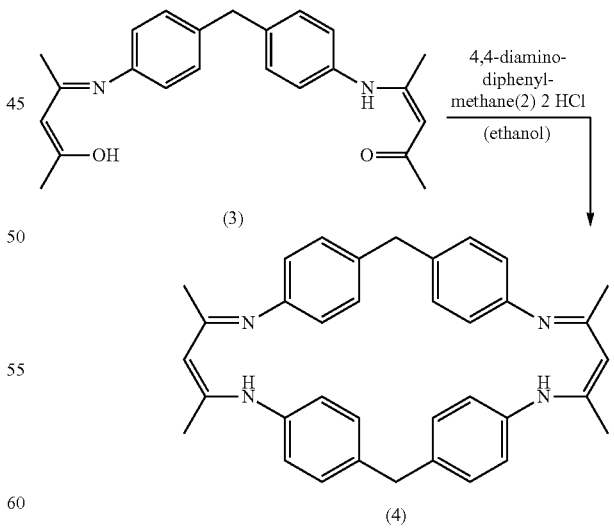

The compound of the formula (3) (1.05 g, 2.90 mmol, 1.0 eq.) and 4,4-diaminodiphenylmethane 2 HCl (0.79 g, 2.90 mmol, 1.0 eq.) are dissolved in ethanol (70.08 ml). Subsequently heated to 80° C. and stirred overnight (for 16 hours). The yellow precipitate is dissolved in water and the amine is released by addition of NaHCO₃ solution and extracted with methylene chloride. After recrystallization in toluene, a solid (compound (4) (35%) is obtained.

|  | Molar mass [g/mol] | Mass [g] | Volume [mL] | Amount [mmol] | Molar equivalents |
|---|---|---|---|---|---|
| Compound of the formula (3) | 362.46 | 1.05 |  | 2.90 | 1.00 |
| 4,4-diamino-diphenylmethane | 271.19 | 0.79 |  | 2.90 | 1.00 |
| ethanol |  |  | 70.08 |  |  |

$^1$H NMR (CDCl$_3$, 298.7 K, 300.13 MHz): δ=13.19 (s, 2H), 6.99 (d, $^3$J=8.3 Hz, 4H), 6.71 (d, $^3$J=8.3 Hz, 4H), 4.83 (s, 2H), 3.77 (s, 4H), 2.06 (s, 12H).

3rd Stage: Complexion with [bis(bis(trimethylsilyl)amido)]zinc

Compound (4) from stage 2 (0.05 g, 0.10 mmol, 1.0 eq.) is dissolved in toluene (50.0 ml), then [bis(bis(trimethylsilyl)amido)]zinc (0.075 ml, 0.19 mmol, 2.0 eq.) is added and the mixture is stirred at 90° C. for 24 h. The clear solution is dried under reduced pressure, and compound (5) is obtained as a solid (55%).

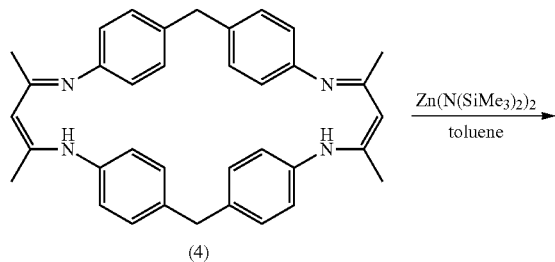

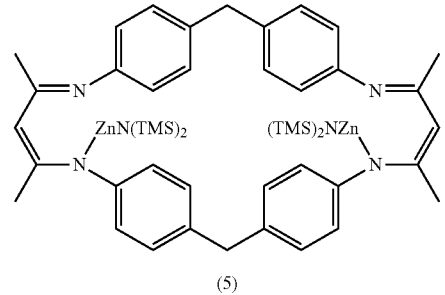

|  | Molar mass [g/mol] | Density [g/cm³] | Mass [g] | Volume [mL] | Amount [mmol] | Molar equivalents |
|---|---|---|---|---|---|---|
| Compound of the formula (4) | 524.7 |  | 0.05 |  | 0.10 | 1.00 |
| Zn(N(SiMe₃)₂)₂ | 386.16 | 0.975 | 0.07 | 0.075 | 0.19 | 2.00 |
| toluene |  |  |  | 70.08 |  |  |

1H NMR(C₆D₆, 298.7 K, 300.13 MHz): δ=6.82 (m 16H), 4.77 (s 2H), 3.55 (s 4H), 1.87 (s 12H), 0.20 (m 38H).

Example 2

Polymerization Tests 2.1 Poly(cyclohexene carbonate)

The dinuclear zinc catalyst from example 1 (21 mg, 0.025 mmol, 0.1 mol %) is dissolved in cyclohexene oxide (2.50 ml, 24.75 mmol, 1.00 eq.). The reactor is placed under carbon dioxide (10 bar) at 100° C. After 1 h, the reaction is stopped by adding methanol (10.0 ml), and the precipitate formed is dissolved in CH₂Cl₂. The organic phase is washed with dilute hydrochloric acid and then concentrated. Thereafter, the polymer is precipitated in methanol (300.0 ml). 2.23 g of poly(cyclohexene carbonate) are obtained.

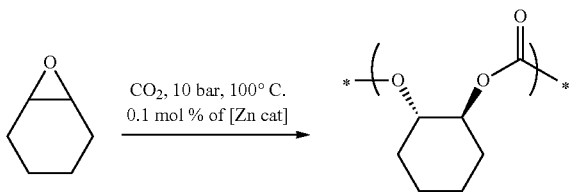

Zn cat=zinc catalyst (5) from example 1

|  | Molar mass [g/mol] | Density [g/cm³] | Mass [g] | Volume [mL] | Amount [mmol] | Molar equivalents |
|---|---|---|---|---|---|---|
| Cyclohexene oxide | 98.14 | 0.972 | 2.43 | 2.50 | 24.75 | 1.00 |
| Zn cat¹⁾ | 839.75 |  | 0.021 |  | 0.025 | 0.001 |

¹⁾Zn cat = zinc catalyst (5) from example 1

$^1$H NMR (CDCl$_3$, 298.7 K, 300.13 MHz): δ=4.75 (s 2H), 1.25-2.25) m 8H).

2.2 Poly(propylene carbonate)

The dinuclear zinc catalyst (5) from example 1 (60.0 mg, 0.072 mmol, 0.1 mol %) is dissolved in propylene oxide (5.00 ml, 71.50 mmol, 1.0 eq.). The reactor is placed under carbon dioxide (30 bar) at 80° C. After 1 h, the reaction is stopped by adding methanol (10.0 ml), and the precipitate formed is dissolved in CH₂Cl₂. The organic phase is washed with dilute hydrochloric acid and then concentrated. Thereafter, the polymer is precipitated in methanol (300.0 ml). Poly(propylene carbonate) (PPC) and propylene carbonate (PC) are obtained.

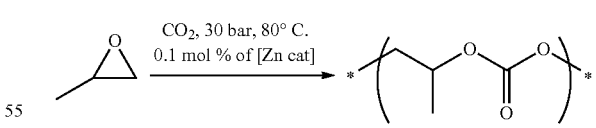

Zn cat=zinc catalyst (5) from example 1

|  | Molar mass [g/mol] | Density [g/cm³] | Mass [g] | Volume [mL] | Amount [mmol] | Molar equivalents |
|---|---|---|---|---|---|---|
| Propylene oxide | 58.4 | 0.830 | 4.15 | 5.00 | 71.5 | 1.00 |
| Zn cat¹⁾ | 839.75 |  | 0.060 |  | 0.072 | 0.001 |

$^{1)}$Zn cat = zinc catalyst (5) from example 1

$^1$H NMR (CDCl$_3$, 298.7 K, 300.13 MHz) (PPC): δ=5.06-4.92 (m 1H), 4.18 (m 2H), 1.31 (d 3H). (PPC).

$^1$H NMR (CDCl$_3$, 298.7 K, 300.13 MHz) (PC): δ=4.82 (m 1H), 4.55 (t 1H), 4.02 (t 1H), 1.47 (d 3H). (PC).

The invention claimed is:

1. An uncharged macrocyclic dimetallic complex of the general formula (V)

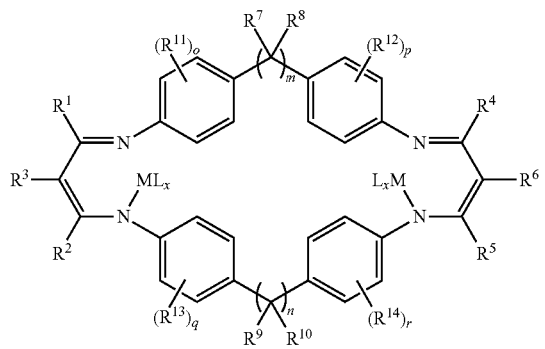

(V)

in which
- $R^1$, $R^2$, $R^4$ and $R^5$ are each independently H, $C_1$-$C_{10}$-alkyl, $C_1$-$C_{10}$-fluoroalkyl, $C_6$-$C_{20}$-fluoroaryl, $C_1$-$C_{10}$-alkoxy or $C_6$-$C_{20}$-aryl;
- $R^3$ and $R^6$ are each independently H, $C_1$-$C_{10}$-alkyl, halogen radical, pseudohalogen radical, carboxylic ester radical, carboxylic ester radical, sulfonyl group or $C_6$-$C_{20}$-aryl;
- $R^7$, $R^8$, $R^9$ and $R^{10}$ are each independently H, $C_1$-$C_{10}$-alkyl, $C_1$-$C_{10}$-fluoroalkyl, $C_1$-$C_{10}$-alkoxy or $C_6$-$C_{20}$-aryl;
- $R^{11}$, $R^{12}$, $R^{13}$ and $R^{14}$ are each independently H, $C_1$-$C_{10}$-alkyl, $C_1$-$C_{10}$-fluoroalkyl, $C_6$-$C_{20}$-aryl, halogen, pseudohalogen, $C_1$-$C_{10}$-alkoxy- or $C_6$-$C_{20}$-aryloxy;
- m, n are each independently 1 to 20;
- o, p, q and r are each independently 0, 1, 2, 3 or 4;
- M is a metal of group 6, 8, 9, 10, 11 or 12 of the periodic table of the elements (IUPAC nomenclature);
- L is a monodentate, singly negatively charged ligand;
- x, depending on the oxidation state and coordination number of the metal M, is 0, 1, 2 or 3.

2. An uncharged macrocyclic dimetallic complex according to claim 1, wherein
- M is Zn;
- L is —N(SiMe$_3$)$_2$, —OAc, OR$^{15}$, —SO$_2$R$^{15}$, halogen, such as F, Cl or Br, or hydrogen;
- R$^{15}$ is $C_1$-$C_{10}$-alkyl or $C_6$-$C_{20}$-aryl; and
- x is 1.

3. A process for preparing an uncharged macrocyclic dimetallic complex according to claim 1 comprising preparing a macrocycle of the general formula (I)

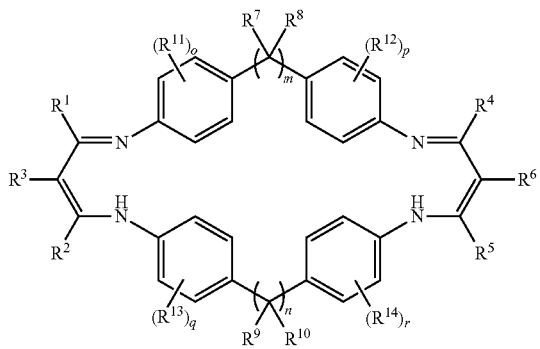

(I)

in which:
- $R^1$, $R^2$, $R^4$ and $R^5$ are each independently H, $C_1$-$C_{10}$-alkyl, $C_1$-$C_{10}$-fluoroalkyl, $C_6$-$C_{70}$-fluoroaryl, $C_1$-$C_{10}$-alkoxy or $C_o$-$C/_o$-aryl;
- $R^3$, $R^6$ are each independently H, $C_1$-$C_{10}$-alkyl, halogen radical, pseudohalogen radical, carboxylic ester radical, sulfonyl group or $C_6$-$C_{20}$-aryl;
- $R^7$, $R^8$, $R^9$ and $R^{10}$ are each independently H, $C_1$-$C_{10}$-alkyl, $C_1$-$C_{10}$-fluoroalkyl, $C_1$-$C_{10}$-alkoxy or $C_6$-$C_{20}$-aryl;
- $R^{11}R^{12}$, $R^{13}$, and $R^{14}$ are each independently H, $C_1$-$C_{10}$-fluoroalkyl, $C_6$-$C_{20}$-aryl, halogen, pseudohalogen, $C_1$-$C_{10}$-alkoxy or $C_6$-$C_{20}$-araryloxy;
- m, n are each independently 1 to 20;
- o, p, q and r are each 0, 1, 2, 3 or 4 by:
i) reacting β-diketones of the formulae (IIa) and (IIb)

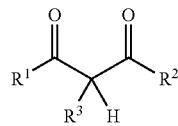

(IIa)

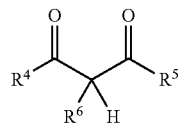

(IIb)

with a diamino compound of the formula (IIIa)

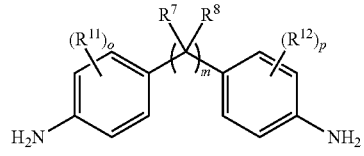

(IIIa)

to obtain a product of the formula (IV)

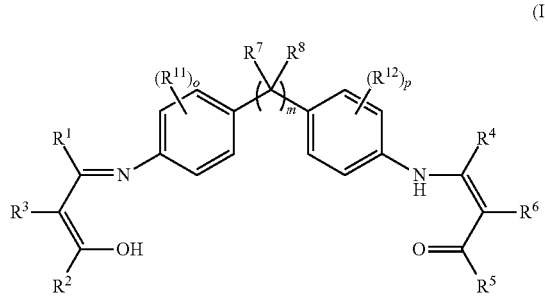
(IV)

ii) reacting the product of the formula (IV) with a compound of the formula (IIb)

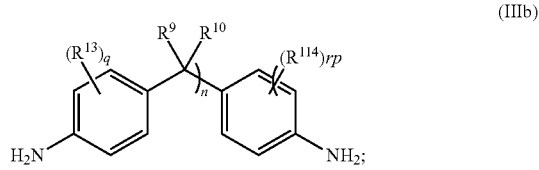
(IIIb)

and reacting the macrocycle of the formula (I) with a metal compound of the general founula (VI)

$$M(L_x)_2 \quad (VI)$$

in which
- M is a metal of group 6, 8, 9, 10, 11 or 12 of the periodic table of the elements (IUPAC nomenclature);
- L is a monodentate, singly negatively charged ligand;
- x is 0, 1, 2 or 3.

4. A process for preparing polycarbonates by reacting carbon dioxide with one or more epoxides in the presence of an uncharged macrocyclic dimetallic complex of the formula (V) according to claim 1.

5. The process according to claim 4, wherein the epoxide(s) is/are selected from the group consisting of ethylene oxide, propylene oxide, butylene oxide, cyclopentene oxide, cyclohexene oxide, cycloheptene oxide, 2,3-epoxypropyl phenyl ether, epichlorohydrin, epibromohydrin, i-butene oxide, styrene oxide, glycidyl ether, glycidyl ester and acryloyl oxides.

6. The process according to claim 5, wherein propylene oxide and/or cyclohexene oxide is/are used as epoxides.

7. A polycarbonate prepared by a process according to claim 4.

8. A polycarbonate according to claim 7, which is a polycarbonate selected from the group consisting of polypropylene carbonate, polycyclohexene carbonate and poly(propylene-cyclohexene).

* * * * *